US00PP13833P29

(12) United States Plant Patent
Dümmen

(10) Patent No.: US PP13,833 P2
(45) Date of Patent: May 20, 2003

(54) NEW GUINEA IMPATIENS PLANT NAMED 'DUEPETHORO'

(75) Inventor: Marga Dümmen, Rheinberg (DE)

(73) Assignee: Dümmen Jungpflanzen GbR, Rheinberg (DE)

( * ) Notice: Subject to any disclaimer, the term of this patent is extended or adjusted under 35 U.S.C. 154(b) by 0 days.

(21) Appl. No.: 10/104,371

(22) Filed: Mar. 22, 2002

(51) Int. Cl.[7] ..... A01H 5/00
(52) U.S. Cl. ..... Plt./318
(58) Field of Search ..... Plt./318

(56) References Cited

U.S. PATENT DOCUMENTS

PP12,094 P2 * 9/2001 Danziger

PP12,353 P2 * 1/2002 Jorna

OTHER PUBLICATIONS

UPOV–ROM GTITM Computer Database, 2002/04, GTI Jouve Retrieval Software, citation for 'Duepethoro'.*

* cited by examiner

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of New Guinea Impatiens plant named 'Duepethoro', characterized by its upright, rounded and uniform plant habit; freely branching and freely flowering habit; red purple-colored flowers that are positioned above and beyond the leaves; and dark green-colored leaves.

1 Drawing Sheet

BOTANICAL CLASSIFICATION/CULTIVER DENOMINATION

*Impatiens hawkeri* cultivar Duepethoro.

BACKGROUND OF THE INVENTION

The present Invention relates to a new and distinct cultivar of New Guinea Impatiens plant, botanically known as *Impatiens hawkeri*, and hereinafter referred to by the name 'Duepethoro'.

The new Impatiens is a product of a planned breeding program conducted by the Inventor in Rheinberg, Germany. The objective of the breeding program is to develop freely branching New Guinea Impatiens cultivars that flower early and have large flowers.

The new Impatiens originated from a cross-pollination made by the Inventor in 1996 of a proprietary selection of *Impatiens hawkeri* identified as code number F-01-14, not patented, as the female, or seed parent, with a proprietary selection of *Impatiens hawkeri* identified as code number S-18-01, not patented, as the male, or pollen parent. The cultivar Duepethoro was discovered and selected by the Inventor as a flowering plant within the progeny of the stated cross-pollination in a controlled environment in Rheinberg, Germany in 1997.

Asexual reproduction of the new cultivar by terminal cuttings taken in Rheinberg, Germany since 1998, has shown that the unique features of this new Impatiens are stable and reproduced true to type in successive generations.

SUMMARY OF THE INVENTION

The following traits have been repeatedly observed and are determined to be the unique characteristics of 'Duepethoro'. These characteristics in combination distinguish 'Duepethoro' as a new and distinct Impatiens cultivar:

1. Upright, rounded and uniform plant habit.
2. Freely branching and freely flowering habit.
3. Red purple-colored flowers that are positioned above and beyond the leaves.
4. Dark green-colored leaves.

Plants of the new Impatiens can be compared to plants of the female parent, the selection F-01-14. In side-by-side comparisons conducted in Rheinberg, Germany, plants of the new Impatiens differed from plants of the selection F-01-14 in the following characteristics:

1. Plants of the new Impatiens were more freely flowering than plants of the selection F-01-14.
2. Flowers of plants of the new Impatiens were darker red purple in color than flowers of plants of the selection F-01-14.

Plants of the new Impatiens can be compared to plants of the male parent, the selection S-18-01. In side-by-side comparisons conducted in Rheinberg, Germany, plants of the new Impatiens differed from plants of the selection S-18-01 in the following characteristics:

1. Plants of the new Impatiens were more compact than plants of the selection S-18-01.
2. Flowers of plants of the new Impatiens were brighter red purple in color than flowers of plants of the selection S-18-01.

Plants of the new Impatiens can also be compared to plants of the cultivar Manado, not patented. In side-by-side comparisons conducted in Rheinberg, Germany, plants of the new Impatiens differed from plants of the cultivar Manado in the following characteristics:

1. Plants of the new Impatiens were larger than plants of the cultivar Manado.
2. Plants of the new Impatiens were more freely branching than plants of the cultivar Manado.
3. Plants of the new Impatiens were more freely flowering than plants of the cultivar Manado.

4. Plants of the new Impatiens had larger flowers than plants of the cultivar Manado.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Colors in the photograph may differ from the color values cited in the detailed botanical description which accurately describe the colors of the new Impatiens. The photograph comprises a side perspective view of a typical flowering plant of 'Duepethoro' grown in a container.

DETAILED BOTANICAL DESCRIPTION

The cultivar Duepethoro has not been observed under all possible environmental conditions. The phenotype may vary somewhat with variations in environment such as temperature and light intensity without, however, any variance in genotype.

The aforementioned photograph and following observations and measurements describe plants grown in Rheinberg, Germany during the spring, under commercial practice in a glass-covered greenhouse. Plants were about 16 weeks from cuttings and were grown in 12-cm containers. During the production of the plants, day and night temperatures averaged 18° C. and light levels were about 4,500 lux.

In the following description, color references are made to The Royal Horticultural Society Colour Chart, 1995 Edition, except where general terms of ordinary dictionary significance are used.

Botanical classification: *Impatiens hawkeri* cultivar Duepethoro.

Parentage:

*Female parent.*—Propietary selection of *Impatiens hawkeri* identified as code number F-01-14, not patented.

*Male parent.*—Proprietary selection of *Impatiens hawkeri* identified as code number S-18-01, not patented.

Propagation:

*Type cutting.*—Terminal cuttings.

*Time to initiate roots.*—Summer: About 7 days at 22° C. Winter: About 10 days at 22° C.

*Time to produce a rooted cutting.*—Summer: About 18 days at 22° C. Winter: About 25 days at 22° C.

*Root description.*—Fine, fibrous and white in color.

*Rooting habit.*—Freely branching.

Plant description:

*General appearance.*—Upright, rounded and uniform plant growth habit; freely branching and flowering habit. Moderately vigorous.

*Crop time.*—From unrooted cuttings, about 16 weeks are required to produce finished flowering plants in 12-cm containers.

*Plant height.*—About 19 cm.

*Plant diameter or spread.*—About 32 cm.

*Lateral branches.*—Quantity per plant: About 15. Length: About 16.5 cm. Diameter: About 8 mm. Internode length: About 4.1 cm. Color: 177A.

*Foliage description.*—Arrangement: Opposite or in whorls. Length: About 9.8 cm. Width: About 3 cm. Shape: Ovate. Apex: Apiculate. Base: Obtuse. Margin: Serrulate with ciliation. Texture, upper and lower surfaces: Smooth, glabrous; leathery. Venation pattern: Pinnate. Color: Young and fully expanded foliage, upper surface: 139A. Young and fully expanded foliage, lower surface: 147B. Venation, upper surface: 144B. Venation, lower surface: 59B.

*Petiole.*—Length: About 3.4 cm. Diameter: About 2.5 mm. Texture, upper and lower surfaces: Smooth, glabrous. Color, upper and lower surfaces: 59B.

Flower description:

*Flower type and flowering habit.*—Single red purple-colored flowers. Freely and continuously flowering; usually about eight flowers and flower buds per lateral branch. Flowers positioned above and beyond the foliage and typically face upward or outward. Petals self-cleaning; gynoecium persistent. Flowers not fragrant.

*Flower longevity.*—Flowers last about one week on the plant.

*Flowering season.*—Year-round under greenhouse conditions; in the garden, flowering from spring until fall. Plants begin flowering about eight weeks after planting.

*Flower buds.*—Length: About 1.6 cm. Diameter: About 1.2 cm. Shape: Ovoid. Color: 59A.

*Flower diameter.*—About 7.6 by 6 cm.

*Flower depth.*—About 9 mm.

*Flower shape.*—Somewhat rounded; mostly flat to slightly cupped.

*Petals.*—Quantity: Five per flower, imbricate. Length: About 3.2 cm. Width: About 4 cm. Shape: Obcordate. Apex: Emarginate, lobed. Base: Acute. Margin: Entire. Texture, upper and lower surfaces: Smooth; satiny. Color: When opening and fully opened, upper surface: 67A; color does not fade with subsequent development. When opening and fully opened, lower surface: 67B.

*Spur.*—Quantity: One per flower. Length: About 4.7 cm. Diameter: At apex: Less than 1 mm. At flower: About 2.5 mm. Aspect: Curved downward. Color: 59A.

*Peduncles.*—Length: About 5 cm. Diameter: About 1 mm. Strength: Moderately strong; flexible. Color: 59A.

*Reproductive organs.*—Androecium: Stamen quantity/arrangement: Five fused at anthers, hooded; filaments free. Anther length: About 5 mm. Anther shape: Oval. Anther color: 61C. Pollen amount: Abundant. Pollen color: 11D. Gynoecium: Pistil quantity: One per flower. Pistil length: About 5 mm. Stigma color: 145D. Style length: Less than 1 mm. Style color: 145D. Ovary arrangement: Five-celled. Ovary color: 146A.

*Seeds/fruits.*—Seed and fruit development has not been observed.

Disease/pest resistance: Plants of the new Impatiens have not been observed to be resistant to pathogens and pests common to Impatiens.

Temperature tolerance: Plants of the new Impatiens have been observed to be tolerant to temperatures ranging from 8 to 35° C.

It is claimed:

1. A new and distinct cultivar of New Guinea Impatiens plant named 'Duepethoro', as illustrated and described.

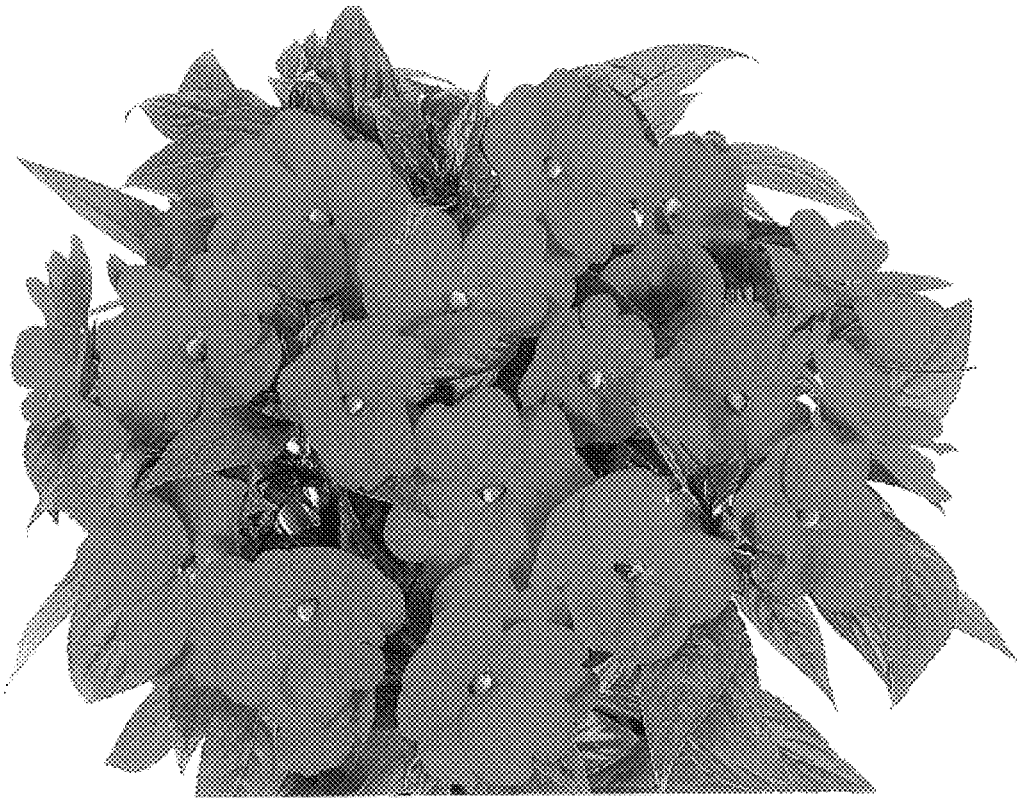

* * * * *